United States Patent [19]

Burns

[11] 4,443,572
[45] Apr. 17, 1984

[54] POLYOLEFIN STABILIZERS

[75] Inventor: Lyle D. Burns, Bartlesville, Okla.

[73] Assignee: Phillips Petroleum Company, Bartlesville, Okla.

[21] Appl. No.: 421,224

[22] Filed: Sep. 22, 1982

[51] Int. Cl.$^3$ .............................................. C08K 5/36
[52] U.S. Cl. .................................... 524/120; 252/407; 524/304; 524/349; 524/350; 524/433
[58] Field of Search ................ 252/407; 524/120, 304, 524/349, 350, 433, 927 R

[56] References Cited

U.S. PATENT DOCUMENTS

| | | | |
|---|---|---|---|
| 3,039,993 | 6/1962 | Friedman | 260/45.8 |
| 3,188,298 | 6/1965 | Williamson et al. | 524/151 |
| 3,244,650 | 4/1966 | Hecker | 524/151 |
| 3,356,617 | 12/1967 | Juredine | 252/400 |
| 3,386,948 | 6/1968 | Needham et al. | 260/41 |
| 3,409,587 | 11/1968 | Mills | 524/151 |
| 3,553,298 | 1/1971 | Hodan | 260/989 |
| 3,639,518 | 2/1972 | Davies et al. | 524/433 |
| 3,856,726 | 12/1974 | Menzel et al. | 524/433 |
| 3,922,249 | 11/1975 | Mills | 524/120 |
| 3,988,298 | 10/1976 | Mills | 260/45.8 |

FOREIGN PATENT DOCUMENTS 56-10535 2/1981 Japan .

OTHER PUBLICATIONS

F. Mitterhofer; "Processing Stability of Polyolefins", Polymer Engineering & Science, Mid-Jul., 1980, vol. 20, No. 10, pp. 692–695.

Primary Examiner—Veronica P. Hoke

[57] ABSTRACT

A stabilizer system for $C_2$ to $C_8$ olefin polymers is provided which comprises at least one pentaerythritol phosphite compound and at least one alkaline earth metal oxide. In addition, stabilized polyolefins are disclosed which contain the above-described stabilizing system.

20 Claims, No Drawings

POLYOLEFIN STABILIZERS

This invention relates to stabilizers for polyolefins. This invention also relates to a method for producing stabilized polyolefins.

It is known that polymers of monoolefins such as polyethylene generally contain a stabilizer system to prevent degradation of the polymer during processing. Such degradation can be due to temperature, light, moisture, or an acidic environment. In certain instances, though, these stabilizers themselves undergo degradation and hence affect their ability to impart the desired stabilization of the polyolefins.

Pentaerythritol phosphite compounds are one class of compounds well known in the art as stabilizers for polyolefins. They provide excellent color stability as well as suppress odors. However, certain pentaerythritol phosphite compounds have been found to be very sensitive to moisture and consequently undergo degradation at high temperatures. This results in black specs in the polyolefin commonly referred to as char. As a result, the usefulness of these phosphite compounds is drastically diminished despite their otherwise excellent performance as color stabilizers. Consequently, stabilizer systems which contain pentaerythritol phosphites which do not degrade would be highly desirable.

Therefore, it is an object of this invention to provide an improved polyolefin stabilizer system. Another object of this invention is to provide stabilized polyolefins.

These and other objects of this invention will become apparent to one skilled in the art from the following detailed description and the appended claims.

In accordance with one embodiment of the present invention, I have discovered that the addition of at least one alkaline earth metal oxide to a stabilizing system comprising at least one pentaerythritol phosphite compound prevents degradation of the latter.

In accordance with another embodiment of the present invention, I have discovered that polyolefins comprising the above stabilizing system do not exhibit char formation.

The pentaerythritol phosphite compounds useful in the present invention are those described by the generic formula:

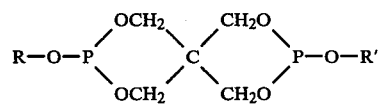

wherein R and R' are the same or different selected from the group consisting of alkyl, cycloalkyl, aryl, aralkyl, alkoxyalkyl, the halo-substituted derivatives thereof containing from one to 20 carbon atoms.

Examples include:
3,9-di(octadecyloxy)-2,4,8,10-tetraoxa-3,9-diphosphaspiro [5.5] undecane (distearyl pentaerythritol diphosphite);
3,9-di(phenoxy)-2,4,8,10-tetraoxa-3,9-diphosphaspiro [5.5] undecane (diphenyl pentaerythritol diphosphite);
3,9-di(methoxy)-2,4,8,10-tetraoxa-3,9-diphosphaspiro [5.5] undecane;
3,9-di(cyclohexyloxy)-2,4,8,10-tetraoxa-3,9-diphosphaspiro [5.5] undecane;
3-phenoxy-9-isodecyloxy-2,4,8,10-tetraoxa-3,9-diphosphaspiro [5.5] undecane;
3,9-di(o-chlorophenoxy)-2,4,8,10-tetraoxa-3,9-diphosphaspiro [5.5] undecane;
3-methoxyethyl-9-isodecyloxy-2,4,8,10-tetraoxa-3,9-diphosphaspiro [5.5] undecane;
and mixtures thereof.

The metal oxides useful in this invention are oxides of the Group IIA alkaline earth metals. MgO and CaO are preferred.

Other ingredients may optionally be present in the stabilizer system also. For example, hindered phenols that can be used as thermal stabilizers and antioxidants are known in the art and can be represented by the general formula:

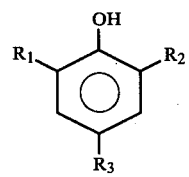

wherein $R_1$, $R_2$, and $R_3$ are alkyl, cycloalkyl, aryl, or arylalkyl groups having up to 10 carbon atoms per group.

Representative examples include:
2,6-di-t-butyl-4-methylphenol;
octadecyl[(3-(3,5-di-t-butyl-4-hydroxyphenyl)] propionate;
di-n-octadecyl(3,5-di-t-butyl-4-hydroxybenzyl) phosphonate;
tetrakis[methylene(3,5-di-t-butyl-4-hydroxyhydrocinnamate)] methane;
1,3,5-trimethyl-2,4,6-tris(3,5-di-t-butyl-4-hydroxybenzyl) benzene;
and mixtures thereof.

In the present invention, 2,6-di-t-butyl-4-methylphenol is preferred.

Thioester compounds which are useful as components in stabilizer systems are represented by the structural formula:

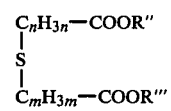

wherein R" and R''' are alkyl groups containing 6 to 24 carbon atoms and n and m are integers from 1 to 6, preferably 2.

Examples include:
laurylhexylthiodipropionate;
dilaurylthiodipropionate;
butylstearylthiodipropionate;
2-ethylhexyllaurylthiodipropionate;
di-2-ethylhexylthiodipropionate;
diisodecylthiodipropionate;
isodecyltetradecylthiodiheptanoate;
laurylstearylthiodipropionate;
distearylthiodipropionate;
hexyltetracosylthiodiacetate;
octyltetradecylthiodibutyrate;
heptylheptadecylthiodiheptanoate;
the 1-lauryl-8-stearyl diester of 4-thiaoctanedioic acid;

the 1-hexyl-10-tetracosyl diester of 3-thiadecanedioic acid;

and mixtures thereof.

The stabilizer system contains both the alkaline earth oxides and the phosphite compound such that the amount by weight of the alkaline earth oxide present relative to the amount by weight of the phosphite compound present will be from about 1.0:1.0 to about 20:1.0.

In addition, the stabilizer system may contain the hindered phenol and thioester such that the amount by weight of the latter two individually relative to the amount by weight of the phosphite compound is in the range of from 0.01:1.0 to about 0.5:1.0.

In the stabilized polyolefin, the phosphite should be present in an amount from about 0.02 to about 5.0 weight percent of the polyolefin composition and the alkaline earth oxide should be present in an amount from about 0.04 to about 10.0 weight percent of the polyolefin composition. The hindered phenol and thioester may be present in an amount ranging individually from 0 to about 1.0 weight percent based on the total weight of the polyolefin.

The olefin polymers for which these stabilizers are useful include homopolymers and copolymers of monoolefins containing 2 to 8 carbon atoms per molecule such as low-density and high-density polyethylene, polypropylene, ethylene-propylene copolymers, polybutylene, ethylene-butylene copolymers, hexene copolymers and the like.

The stabilizer system is added to the olefin polymers in any conventional manner. This includes dry blending or spraying solutions of the ingredients onto resin powder or pellets followed by melt blending of the mixture in an extruder, on a roll mill, in a Bandbury mixer and the like. Addition of the stabilizer to the polymer melt followed by mixing process can also be practiced. Whatever method is used, a stabilizing amount of the stabilizer system should be added to the olefin polymer. A stabilizing amount is defined to be that amount of the stabilizer system which needs to be added to the particular polyolefin to prevent the latter's degradation.

Other additives including fillers, pigments, antistatic agents and the like can also be added to the olefin polymer.

The olefin polymer composition protected by the stabilizer systems of this invention are useful for formation by extrusion, injection molding, blow molding and the like into a variety of molded objects.

The following examples illustrate the present invention.

EXAMPLES

Example I

HHM 4903 polyethylene (PE) fluff (ASTM D1505 density: about 0.949 g/cc; ASTM D1238 melt index: about 0.57 g/10 minutes; marketed by Phillips Chemical Company, Bartlesville, Oklahoma) was dry-blended with various stabilizers in a high speed Waring blender, followed by tumble mixing in a Norton jar rolling mill for 10 minutes. The blended formulations were extruded on a ¾-inch Brabender Plasticorder extruder (L/D ratio=25:1), at a screw speed of 30 rpm and an extruder barrel temperature of about 550° F.

The prepared PE/stabilizer blends were examined for thermal stability by placing said blends in 10×75 mm test tubes, that were slowly heated in an electrical heating block connected with a Variac potentiometer to about 550° F., which required approximately 1 hour, and were then kept at this temperature for about 1–2½ hours. The formulation of black specks (char) due to the degradation of stabilizers was recorded.

The color stability of polyethylene/stabilizer blends was determined by means of a Hunter Lab Color Difference Meter 25 DM using ¼×2¼ inch discs that were compression molded, after preheating for 2 minutes, at 350° F. (177° C.)/30 tons during a time period of 2 minutes, and were then allowed to cool for about 10 minutes.

The color evaluation was based on three tristimulus reflectance values (a, b and L) defined as follows:

$-a = \text{green} \longleftrightarrow +a = \text{red}$ $-b = \text{blue} \longleftrightarrow +b = \text{yellow}$ $L = 0, \text{black} \longleftrightarrow L = 100, \text{white}.$ These three values were mathematically weighted in the equation for the Color Number=b(0.0382L−0.0056a−0.3374b). The b value had the greatest weight in this expression, and as the b value became more positive (indicating a more intense yellow color), generally the Color Number decreased.

Example II

Results of thermal and color stability measurements as outlined in Example I for PE/stabilizer blends prepared in accordance with the procedure described in Example I are summarized in Table I, and Table II.

TABLE I

| Run | Heating Time At 550° F. | BHT[1] (Wt %) | DLTDP[2] (Wt %) | Weston 618[3] (Wt %) | CaO (Wt %) | MgO (Wt %) | Observation |
|---|---|---|---|---|---|---|---|
| 1 (Control) | 1 Hour | 0.05 | 0.03 | — | — | — | No Char |
| 2 (Control) | 1 Hour | 0.05 | 0.03 | 1.0 | — | — | Charred |
| 3 (Invention) | 1 Hour | 0.05 | 0.03 | 1.0 | 2.0 | — | No Char |
| 4 (Invention) | 1 Hour | 0.05 | 0.03 | 1.0 | — | 2.0 | No Char |
| 5 (Control) | 2½ Hours | 0.05 | 0.03 | 1.0 | — | — | Charred |
| 6 (Invention) | 2½ Hours | 0.05 | 0.03 | 1.0 | 1.0 | — | Slightly Charred |
| 7 (Invention) | 2½ Hours | 0.05 | 0.03 | 1.0 | 2.0 | — | No Char |
| 8 | 2½ Hours | 0.05 | 0.03 | 1.0 | — | 1.0 | No Char |

TABLE I-continued

| Run | Heating Time At 550° F. | BHT[1] (Wt %) | DLTDP[2] (Wt %) | Weston 618[3] (Wt %) | CaO (Wt %) | MgO (Wt %) | Observation |
|---|---|---|---|---|---|---|---|
| (Invention) 9 (Invention) | 2½ Hours | 0.05 | 0.03 | 1.0 | — | 2.0 | No Char |

Footnotes to Table I
[1] 6-di-t-butyl-4-methyl phenol, also called 2,6-di-t-butyl-p-cresol, an antioxidant marketed by Koppers Company, Oil City, PA.
[2] dilauryl thiodipropionate, a stabilizer marketed by Witco Chemical Corporation, Taft, LA.
[3] distearyl pentaerythritol diphosphite, a color stabilizer marketed by Borg-Warner Corporation in Morgantown, W.Va.

TABLE II

| Run | BHT (Wt %) | DLTDP (Wt %) | Weston 618 (Wt %) | ZnO (Wt %) | CaO (Wt %) | MgO (Wt %) | Color b | Parameters Color No. |
|---|---|---|---|---|---|---|---|---|
| 10 (Control) | 0.05 | 0.03 | — | — | — | — | 4.0 | 147 |
| 11 (Control) | 0.05 | 0.03 | 0.05 | — | — | — | 1.3 | 231 |
| 12 (Control) | 0.05 | 0.03 | 0.05 | 0.1 | — | — | 2.9 | 161 |
| 13 (Invention) | 0.05 | 0.03 | 0.05 | — | 0.1 | — | 0.7 | 257 |
| 14 (Invention) | 0.05 | 0.03 | 0.05 | — | — | 0.1 | 1.6 | 211 |

Data in Table I show that amounts of 1-2 parts of either CaO or MgO per 1 part of Weston 618 color stabilizer are effective in suppressing char formation in PE blends caused by the degradation of Weston 618.

Table II shows that CaO and MgO, at amounts of about 2 parts by weight per 1 part by weight of Weston 618, are effective in retaining a low positive b value and high color number (indicating little yellow color), whereas another metal oxide, ZnO, causes a noticeable yellowing of the stabilized PE blend (more positive b, lower Color Number).

Reasonable variations and modifications are possible within the scope of the foregoing disclosure and the appended claims.

I claim:

1. A polymeric composition of at least one polymer of an olefin having 2 to 8 carbon atoms per molecule, having therein a stabilizer system, comprising:
    (a) from 0.1 to 5.0 weight percent of at least one pentaerythritol phosphite compound of the formula:

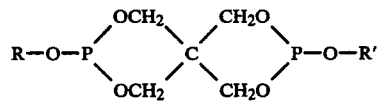

wherein R and R' are the same or different selected from the group consisting of alkyl, cycloalkyl, aryl, alkoxyalkyl, the halo-substituted derivatives thereof containing from one to 20 carbon atoms;
    (b) from 0.1 to 10.0 weight percent of at least one Group IIA alkaline earth metal oxide;
    (c) a hindered phenol of the formula

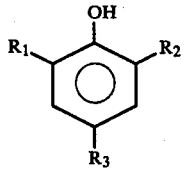

wherein $R_1$, and $R_3$ are alkyl, cycloalkyl, aryl, or arylalkyl groups having up to 10 carbon atoms per group such that said hindered phenol is present in an amount by weight relative to said phosphite compound in the range of from about 0.01:10 to about 0.5:1.0; and
    (d) at least one thioester represented by the general formula

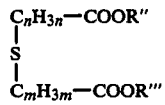

wherein R" and R'" are alkyl groups containing 6 to 24 carbon atoms and n and m are integers from 1 to 6 such that said thioester is present in an amount by weight relative to said phosphite compound in the range of from about 0.01:10 to about 0.5:10.

2. A polymeric composition according to claim 1 wherein said pentaerythyritol phorphite compound is at least one selected from the group consisting of
    3,9-di(octadecyloxy)-2,4,8,10-tetraoxa-3,9-diphosphaspiro [5.5] undecane (distearyl pentaerythritol diphosphite);
    3,9-di(phenoxy)-2,4,8,10-tetraoxa-3,9-diphosphaspiro [5.5] undecane (diphenyl pentaerythritol diphosphite);
    3,9-di(methoxy)-2,4,8,10-tetraoxa-3,9-diphosphaspiro [5.5] undecane;

3,9-di(cyclohexyloxy)-2,4,8,10-tetraoxa-3,9-diphosphaspiro [5.5] undecane;

3-phenoxy-9-isodecyloxy-2,4,8,10-tetraoxa-3,9-diphosphaspiro [5.5] undecane;

3,9-di(o-chlorophenoxy)-2,4,8,10-tetraoxa-3,9-diphosphaspiro [5.5] undecane; and 3-methoxyethyl-9-isodecyloxy-2,4,8,10-tetraoxa-3,9-diphosphaspiro [5.5] undecane.

3. A polymeric composition according to claim 2 wherein said pentaerythritol phosphite compound is distearylpentaerythritol diphosphite.

4. A polymeric composition in accordance to claim 1 wherein said alkaline earth metal oxide is magnesium oxide.

5. A polymeric composition in accordance to claim 1 wherein said alkaline earth metal oxide is calcium oxide.

6. A polymeric composition in accordance to claim 1 wherein said hindered phenol is at least one from the group consisting of 2,6-di-t-butyl-4-methylphenol;

octadecyl[(3-(3,5-di-t-butyl-4-hydroxyphenyl)] propionate;

di-n-octadecyl(3,5-di-t-butyl-4-hydroxybenzyl) phosphonate; tetrakis[methylene(3,5-di-t-butyl-4-hydroxyhydrocinnamate)] methane;

1,3,5-trimethyl-2,4,6-tris(3,5-di-t-butyl-4-hydroxybenzyl) benzene.

7. A polymeric composition in accordance with claim 6 wherein said hindered phenol is 2,6-di-t-butyl-4-methylphenol.

8. A polymeric composition in accordance with claim 1 wherein said thioester compound is at least one from the group consisting of laurylhexylthiodipropionate;
dilaurylthiodipropionate;
butylstearylthiodipropionate; and
2-ethylhexyllaurylthiodipropionate.

9. A polymeric composition according to claim 8 wherein said thioester is dilaurylthiodipropionate.

10. A polymeric composition according to claim 1 wherein said olefin is ethylene.

11. A polymer according to claim 1 wherein said olefin is propylene.

12. A stabilizer system comprising:

(a) at least one pentaerythritol phosphite compound of the formula:

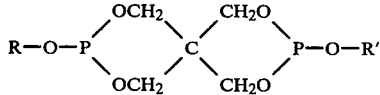

wherein R and R' are the same or different selected from the group consisting of alkyl, cycloalkyl, aryl, alkoxyalkyl, the halo-substituted derivatives thereof containing from one to 20 carbon atoms;

(b) at least one Group IIA alkaline earth metal oxide, such that the amount by weight of (b) present relative to the amount by weight of (a) present is in the range of from about 1.0:1.0 to about 20:1.0;

(c) a hindered phenol of the formula

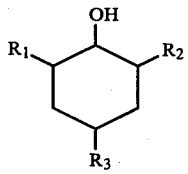

wherein $R_1$, and $R_3$ are alkyl, cycloalkyl, aryl, or arylalkyl groups having up to 10 carbon atoms per group such that said hindered phenol is present in an amount by weight relative to said phosphite compound in the range of from about 0.01:10 to about 0.5:1.0; and (d) at least one thioester represented by the general formula

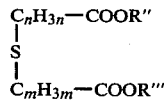

wherein R" and R'" are alkyl groups containing 6 to 24 carbon atoms and n and m are integers from 1 to 6 such that said thioester is present in an amount by weight relative to said phosphite compound in the range of from about 0.01:10 to about 0.5:10.

13. A stabilizer system in accordance with claim 12 wherein said pentaerythritol phosphite compound is at least one selected from the group consisting of 3,9-di(octadecyloxy)-2,4,8,10-tetraoxa-3,9-diphosphaspiro [5.5] undecane (distearyl pentaerythritol diphosphite);

3,9-di(phenoxy)-2,4,8,10-tetraoxa-3,9-diphosphaspiro [5.5] undecane (diphenyl pentaerythritol diphosphite);

3,9-di(methoxy)-2,4,8,10-tetraoxa-3,9-diphosphaspiro [5.5] undecane;

3,9-di(cyclohexyloxy)-2,4,8,10-tetraoxa-3,9-diphosphaspiro [5.5] undecane;

3-phenoxy-9-isodecyloxy-2,4,8,10-tetraoxa-3,9-diphosphaspiro [5.5] undecane;

3,9-di(o-chlorophenoxy)-2,4,8,10-tetraoxa-3,9-diphosphaspiro [5.5] undecane; and 3-methoxyethyl-9-isodecyloxy-2,4,8,10-tetraoxa-3,9-diphosphaspiro [5.5] undecane.

14. A stabilizer system in accordance with claim 13 wherein said pentaerythritol phosphite compound is distearylpentaerythritol diphosphite.

15. A stabilizer system in accordance with claim 12 wherein said alkaline earth metal oxide is magnesium oxide.

16. A stabilizer system in accordance with claim 12 wherein said alkaline earth metal oxide is calcium oxide.

17. A stabilizer system in accordance with claim 12 wherein said hindered phenol is at least one from the group consisting of 2,6-di-t-butyl-4-methylphenol;

octadecyl[(3-(3,5-di-t-butyl-4-hydroxyphenyl)] propionate;

di-n-octadecyl(3,5-di-t-butyl-4-hydroxybenzyl) phosphonate;

tetrakis[methylene(3,5-di-t-butyl-4-hydroxyhydrocinnamate)] methane; and 1,3,5-trimethyl-2,4,6-tris(3,5-di-t-butyl-4-hydroxybenzyl) benzene.

18. A stabilizer system in accordance with claim 17 wherein said hindered phenol is 2,6-di-t-butyl-4-methylphenol.

19. A stabilizer system in accordance with claim 12 wherein said thioester compound is at least one from the group consisting of laurylhexylthiodipropionate;
dilaurylthiodipropionate;
butylstearylthiodipropionate; and
2-ethylhexyllaurylthiodipropionate.

20. A stabilizer system in accordance with claim 19 wherein said thioester is dilaurylthiodipropionate.

* * * * *